United States Patent
Kissos et al.

(10) Patent No.: US 11,961,601 B1
(45) Date of Patent: Apr. 16, 2024

(54) ADAPTIVE USER INTERFACE FOR DETERMINING ERRORS IN PERFORMANCE OF ACTIVITIES

(71) Applicant: AMAZON TECHNOLOGIES, INC., Seattle, WA (US)

(72) Inventors: Imry Kissos, Redmond, WA (US); Joel Wilson Brown, Seattle, WA (US); Ilia Vitsnudel, Even Yehuda (IL); Omer Meir, Seattle, WA (US); Lior Fritz, Seattle, WA (US); Matan Goldman, Redmond, WA (US); Eduard Oks, Redmond, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 869 days.

(21) Appl. No.: 16/919,870

(22) Filed: Jul. 2, 2020

(51) Int. Cl.
| | |
|---|---|
| G16H 20/30 | (2018.01) |
| A63B 24/00 | (2006.01) |
| A63B 71/06 | (2006.01) |
| G06T 19/20 | (2011.01) |
| G06V 20/40 | (2022.01) |
| G06V 40/20 | (2022.01) |
| G09B 19/00 | (2006.01) |

(52) U.S. Cl.
CPC ......... *G16H 20/30* (2018.01); *A63B 24/0006* (2013.01); *A63B 71/0622* (2013.01); *G06T 19/20* (2013.01); *G06V 20/40* (2022.01); *G06V 40/23* (2022.01); *G09B 19/003* (2013.01); *A63B 2024/0009* (2013.01); *A63B 2024/0068* (2013.01); *A63B 2024/0096* (2013.01); *A63B 2071/0647* (2013.01); *A63B 2220/806* (2013.01); *A63B 2220/833* (2013.01); *A63B 2220/836* (2013.01); *G06T 2200/24* (2013.01); *G06T 2219/2016* (2013.01)

(58) Field of Classification Search
CPC ........ G16H 20/30; G06V 20/30; G06V 40/23; A63B 24/0006; A63B 71/0622; A63B 2024/0009; A63B 2024/0068; A63B 2024/0096; A63B 2071/0647; A63B 2220/806; A63B 2220/833; A63B 2220/24; G06T 19/20; G06T 2219/2016
USPC ....................................................... 705/2–3
See application file for complete search history.

(56) References Cited

U.S. PATENT DOCUMENTS

| | | | |
|---|---|---|---|
| 10,726,461 B2 * | 7/2020 | Borucki | ............... H04L 67/131 |
| 2014/0100464 A1 * | 4/2014 | Kaleal | ................... A61B 5/486 |
| | | | 600/595 |

(Continued)

*Primary Examiner* — Michael Tomaszewski
(74) *Attorney, Agent, or Firm* — Lindauer Law, PLLC

(57) ABSTRACT

To assist a user in the correct performance of an activity, video data is acquired. A pose of the user is determined from the video data and an avatar is generated representing the user in the pose. The pose of the user is compared to one or more other poses representing correct performance of the activity to determine one or more differences that may represent errors by the user. Depending on the activity that is being performed, some errors may be presented to the user during performance of the activity, while other errors may be presented after performance of the activity has ceased. To present an indication of an error, a specific body part or other portion of the avatar that corresponds to a difference between the user's pose and a correct pose may be presented along with an instruction regarding correct performance of the activity.

20 Claims, 7 Drawing Sheets

(56) References Cited

U.S. PATENT DOCUMENTS

| | | | | |
|---|---|---|---|---|
| 2015/0037771 | A1* | 2/2015 | Kaleal, III | G16H 50/30 |
| | | | | 434/257 |
| 2015/0038806 | A1* | 2/2015 | Kaleal, III | A61B 5/4833 |
| | | | | 600/301 |
| 2015/0126826 | A1* | 5/2015 | Kaleal, III | A61B 5/11 |
| | | | | 600/300 |
| 2015/0339854 | A1* | 11/2015 | Adler | G16H 20/30 |
| | | | | 345/419 |
| 2016/0086500 | A1* | 3/2016 | Kaleal, III | A61B 5/45 |
| | | | | 434/257 |
| 2018/0315247 | A1* | 11/2018 | Van Andel | G06F 3/017 |
| 2021/0322853 | A1* | 10/2021 | Lockhart | A63B 71/0622 |
| 2022/0072377 | A1* | 3/2022 | Russell | G06V 10/25 |
| 2022/0076666 | A1* | 3/2022 | Trehan | G10L 15/22 |
| 2023/0082953 | A1* | 3/2023 | Berger | G06V 20/44 |

\* cited by examiner

ADAPTIVE USER INTERFACE FOR DETERMINING ERRORS IN PERFORMANCE OF ACTIVITIES

BACKGROUND

When performing an activity, such as a fitness exercise, a user may be provided with video instruction demonstrating proper performance of the activity. If the user performs the activity incorrectly, the specific errors made by the user and the manner in which the user may correct the errors are not always evident.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
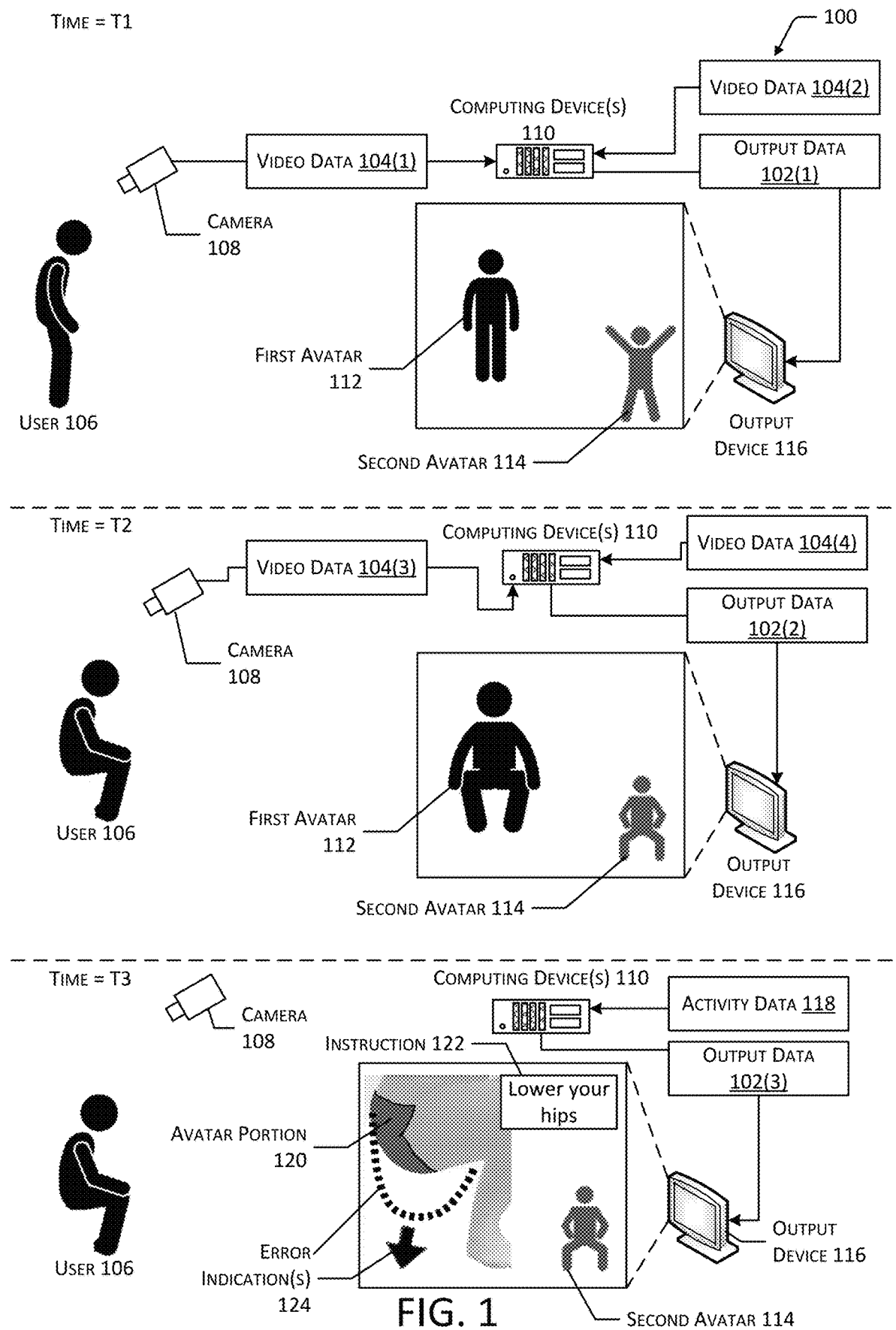
FIG. 1 depicts an implementation of a system for determining a video output to be presented based on acquired video data indicative of a user performing an activity.

While implementations are described in this disclosure by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used in this disclosure are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include", "including", and "includes" mean "including, but not limited to".

DETAILED DESCRIPTION

Video output, as well as other types of output, such as audio or text, may be used to provide instruction to a user for performance of a task. For example, a training video may include instruction for proper performance of fitness or rehabilitation exercises, work-related tasks, and so forth. A user may attempt to perform an activity based on instruction presented in a video. Various types of sensors may be used to determine whether the user correctly performed the activity, or whether the user committed one or more errors in performing the activity. For example, data from a camera that acquires video of the user during performance of the activity may be used to determine the positions of various body parts of the user. If the user commits an error when performing the activity, the user may position one or more body parts in a position that deviates from data indicating a correct position of the body parts. The user may then be provided with instructions or other indications regarding the errors that were detected. In some cases, correcting these errors based on the video output and the instruction provided to the user may be difficult.

Described in this disclosure are techniques for providing a user with specific visual instruction for correcting errors in performance of an activity by presenting a portion of an avatar representing the user's body position. As a user performs an activity within the field of view of a camera, video data is acquired. Based on the video data, a three-dimensional pose (e.g., positions of joints and angles of the joints) of the user is determined. A body shape of the user may also be determined. For example, a frame of video data may be used to determine the position of one or more body parts of the user. The acquired video data is used to generate an avatar representing the pose of the user. The avatar may be presented to the user in conjunction with the video instruction regarding performance of the activity. For example, a first avatar representing the user's body position may be presented adjacent to a video of an instructor or a second avatar demonstrating correct performance of the activity. The user may therefore be able to visually see their position relative to the correct body position demonstrated by the instructor or second avatar.

As the user performs the activity, the pose of the user may be analyzed using data representing correct poses for performance of the activity. Differences between the pose of the user and the correct poses may indicate one or more errors committed by the user. For example, a neural network or other type of machine learning algorithm may use data representing correct poses as inputs to classify the type of error associated with the pose of the user and the severity of the error. Continuing the example, a correct pose may include locations of various body parts, such as a correct position of a user's knees, hips, feet, elbows, and so forth. The user's errors may be classified by determining locations of body parts of the user that differ from the locations of body parts indicated in the correct poses and the extent to which the locations of the user's body parts differ from the correct poses. Based on this analysis, one or more differences between the pose of the user and one or more correct poses may be determined.

Data regarding the activity that is performed by the user may indicate whether a particular difference is to be disregarded, whether corrective instruction is to be presented during performance of the activity, or whether corrective instruction is to be presented after cessation of the activity. Data regarding the activity may also indicate a hierarchy or priority value associated with errors, a maximum number of errors that should be presented, and so forth. For example, if a user is performing a squat exercise, differences regarding the position of the user's wrists may be disregarded, differences regarding the position of the user's hips may result in corrective instruction after completion of the exercise, and differences regarding the position of the user's knees may result in corrective instruction during performance of the exercise. When corrective instruction regarding a difference is presented, a portion of the user's avatar associated with the difference is determined. For example, if an error relates to an incorrect position of the user's hips, a portion of the user's avatar representing the hips of the user may be determined. This portion of the avatar may then be presented to the user, along with an indication of the error, corrective instruction, a correct position of an instructor or second avatar, and so forth. For example, in response to determining an incorrect position of the user's hips, an interface presented to the user may show an enlarged (e.g., zoomed-in) view of the hips of the user's avatar, accompanied by arrows, lines, text, or other indicia indicating the direction in which the hips of the user should be moved. In some implementations, the user interface may receive user input to change the viewpoint presented to the user. For example, a user may provide input to cause a portion of an avatar presented to a user to be magnified, or a viewpoint from which the avatar is presented may be rotated, translated, and so forth. In other implementations, a user may select particular body parts on which to focus. In such a case, information regarding differences associated with those body parts may be preferentially presented. For example, a user may indicate a preference to focus on errors associated with the position of the lower body. In response to this indication, errors associated with the upper body of the user may not be presented or may only be presented if at least a threshold number of errors associated with the lower body are not determined.

By presenting a user with a visual indication of the user's own body position, focused on a specific body part of the user, errors in performance of an activity by the user may be readily recognized and addressed. Particular errors for which corrective instruction is suitable during performance of an activity may be addressed during performance of the activity. Other errors may be addressed after cessation of the activity. For example, after cessation of an activity, a user may be provided with an interface that enables navigation between video clips, each of which addresses an error that occurred during performance of the activity. In some implementations, the errors committed by the user may be used to determine a score regarding performance of the activity by the user.

FIG. 1 depicts an implementation of a system 100 for determining a video output to be presented based on acquired video data 104 indicative of a user 106 performing an activity. At a first time T1, a user 106 may be positioned within a field of view of a camera 108. The camera 108 may acquire video data 104(1) indicative of the pose of the user 106. In some implementations, one or more other types of sensors may also acquire data indicative of the pose of the user 106 or performance of the activity by the user 106. For example, held or wearable sensors, such as accelerometers, gyroscopes, or other types of motion or position sensors may be used to determine motion data, position data, and so forth that indicates the position or movement of portions of the user's body. As another example, sensors that detect the movement or position of the user 106 or another object may also be integrated within objects in the environment. For example, a floor mat may include a sensor that detect a user's position on top of the mat, or a sensor may be associated with an object that may be manipulated by a user 106, such as a piece of fitness or occupational equipment.

One or more servers 110 may receive the video data 104(1) from the camera 108, and in some implementations, data from other sensors associated with the user 106. While FIG. 1 depicts a single server 110, any number and any type of computing devices may be used including, without limitation, personal computing devices, portable computing devices, wearable computing devices, servers, smartphones, set top boxes, and so forth. Additionally, while FIG. 1 depicts a server 110 receiving the video data 104(1) from the camera 108, in other implementations, the video data 104(1) may be processed by a processor or computing device integrated with the camera 108 or by a computing device located in an environment with the camera 108, and use of a separate server 110 may be omitted. In still other implementations, a combination of computing devices in an environment with the camera 108 or user 106 and one or more separate servers 110 may be used.

The server(s) 110 may generate a first avatar 112 representative of the pose of the user 106 based on the video data 104(1). For example, the server(s) 110 may use object recognition and image analysis algorithms to determine a portion of one or more frames of the video data 104(1) that include the user 106, then determine the position of one or more body parts of the user 106. For example, the server(s) 110 may determine the location of particular points within a frame of video data 104(1) that represent the locations and orientations (e.g., angles) of joints or other body parts of the user 106, such as locations of a user's head, shoulders, elbows, knees, and so forth. The location of each point in a set of points that represent a pose may be determined based in part on object recognition and in part on one or more rules that constrain the location of particular points relative to the locations of other points. For example, the determined location of a point representing a user's wrist may be constrained based on the determined location of a point representing a user's elbow, a bone length of the user's arm, an angular range of motion associated with the elbow, and so forth. In cases where the location of a particular body part of the user 106 cannot be determined within a frame of video data 104(1), the location of a representation of that body part in the first avatar 112 may be included by interpolating a location of the body part based on adjacent frames of video data 104(1) or based in part on one or more rules that constrain the location of the body part relative to the locations of one or more other body parts.

The server(s) 110 may also access video data 104(2) that includes instructional content for performance of the activity undertaken by the user. For example, the video data 104(2) may include prerecorded data depicting an instructor, or a second avatar 114, performing a fitness exercise or other activity. Based on the video data 104(1) acquired using the camera and the video data 104(2) that includes instructional content, the server(s) 110 may generate output data 102(1) that presents the first avatar 112, representative of the user 106, adjacent to the second avatar 114, representative of correct performance of the activity. In other implementations, a recorded instructor or other individual may be presented rather than a second avatar 114. The output data 102(1) may be provided to an output device 116 for presentation to the user 106 as a video output. While FIG. 1 depicts the output device 116 as a display device, other types of output, such as audio or haptic output, may also be presented. Additionally, while FIG. 1 depicts a single output device 116, any number of output devices 116 of the same or different types may be used.

For example, at the first time T1, FIG. 1 depicts the user 106 standing in a generally upright position. The video output associated with the output data 102(1) includes the first avatar 112, representing the pose of the user 106, standing in an upright position. The first avatar 112 is shown adjacent to a second avatar 114, determined from the video data 104(2), standing in a generally upright position with raised arms.

The user 106 may perform the activity based on instruction included in the video output. For example, the user 106 may attempt to perform movements demonstrated by the second avatar 114. Presentation of the first avatar 112 that represents the pose of the user 106 adjacent to the second avatar 114 may facilitate recognition by the user 106 of correct and incorrect performance of various portions of the activity.

At a second time T2 subsequent to the first time T1, the camera 108 may acquire additional video data 104(3) indicative of a subsequent pose of the user 106 as the user 106 performs the activity. The server(s) 110 may receive the video data 104(3) from the camera 108. The server(s) 110 may also receive additional video data 104(4) for presenting the second avatar 114. Based on the video data 104(3) from the camera 108 and the video data 104(4) for the second avatar 114, the server(s) may provide additional output data 102(2) to the output device 116 for presentation of a video output. For example, at the second time T2, FIG. 1 depicts the user 106 in a squatting position. The video output associated with the output data 102(2) shows the first avatar 112 in a squatting position, representing the pose of the user 106. The first avatar 112 is shown adjacent to the second avatar 114, which is also shown in a squatting position.

At a third time T3 subsequent to the second time T2, based on the acquired video data 104(3), the server(s) 110 may determine one or more differences between the pose of the user 106 and activity data 118 indicative of one or more poses that correspond to correct performance of the activity. For example, the location of one or more body parts of the user 106, determined based on analysis of the video data 104(3), may be compared to the pose of the second avatar 114, or one or more other poses included in the activity data 118. In some implementations, a neural network or other type of machine learning algorithm may use data representing multiple correct poses as inputs, then classify the differences between the pose of the user 106 and the poses used as inputs. For example, each correct pose included in the activity data 118 may include locations of various body parts relative to other body parts. Differences between the pose of the user 106 and the poses of the activity data 118 may be determined by classifying the type and magnitude of the differences between the pose of the user 106 and the poses of the activity data 118. The differences may be used to determine output data 102(3) to be provided to the output device 116 for presentation of a video output.

For example, the server(s) 110 may determine a body part of the user 106 or a portion of the first avatar 112 that is associated with an identified difference. The server(s) 110 may then generate output data 102(3) for presenting an avatar portion 120 representing the body part of the user 106 that is associated with the difference. For example, FIG. 1 depicts the video output associated with the output data 102(3) including an enlarged view showing an avatar portion 120 representing a position of the hips of the user 106. Based on the activity data 118, the server(s) 110 may also determine one or more instructions 122 to be presented in conjunction with the avatar portion 120. For example, FIG. 1 depicts the video output associated with the output data 102(3) including a text instruction 122 that reads "Lower your hips". In other implementations, instructions 122 may include audio output, haptic output, or other types of output. Based on the activity data 118, the server(s) 110 may also determine one or more error indications 124 to be presented in conjunction with the avatar portion 120. For example, FIG. 1 depicts a first error indication 124 as a directional arrow indicating a direction in which the user 106 should move their hips to achieve a correct pose. FIG. 1 depicts a second error indication 124 as a line indicative of a proper position for the hips. In some implementations, the output data 102(3) may also cause presentation of the second avatar 114 adjacent to the avatar portion 120.

In some implementations, video output associated with a difference between a pose of the user 106 and the activity data 118 may be presented during performance of the activity by the user 106. In other implementations, the video output may be presented after cessation of the activity by the user 106. For example, the activity data 118 may indicate particular differences for which presentation of the video output during performance of the activity is suitable. Based on the activity data 118, such video output may be presented within a threshold length of time after the difference is determined. In cases where the activity data 118 does not indicate that the video output is suitable for presentation during performance of the activity, or where the activity data 118 indicates that the video output is suitable for presentation after cessation of the activity, the video output may be presented in response to determining that the user 106 has ceased performing the activity. Determining cessation of the activity by the user 106 may include determining a lack of movement or participation by the user 106 based on acquired video data 104, completion of the presentation of instructional content, or an indication by the user 106 that performance of the activity has ceased. Determining cessation of the activity may also include determining completion of the activity, such as by determining that the user 106 performed a selected number of repetitions of a fitness exercise according to a repetition counting algorithm or performed the activity for a selected time period associated with the activity.

Figure 2:
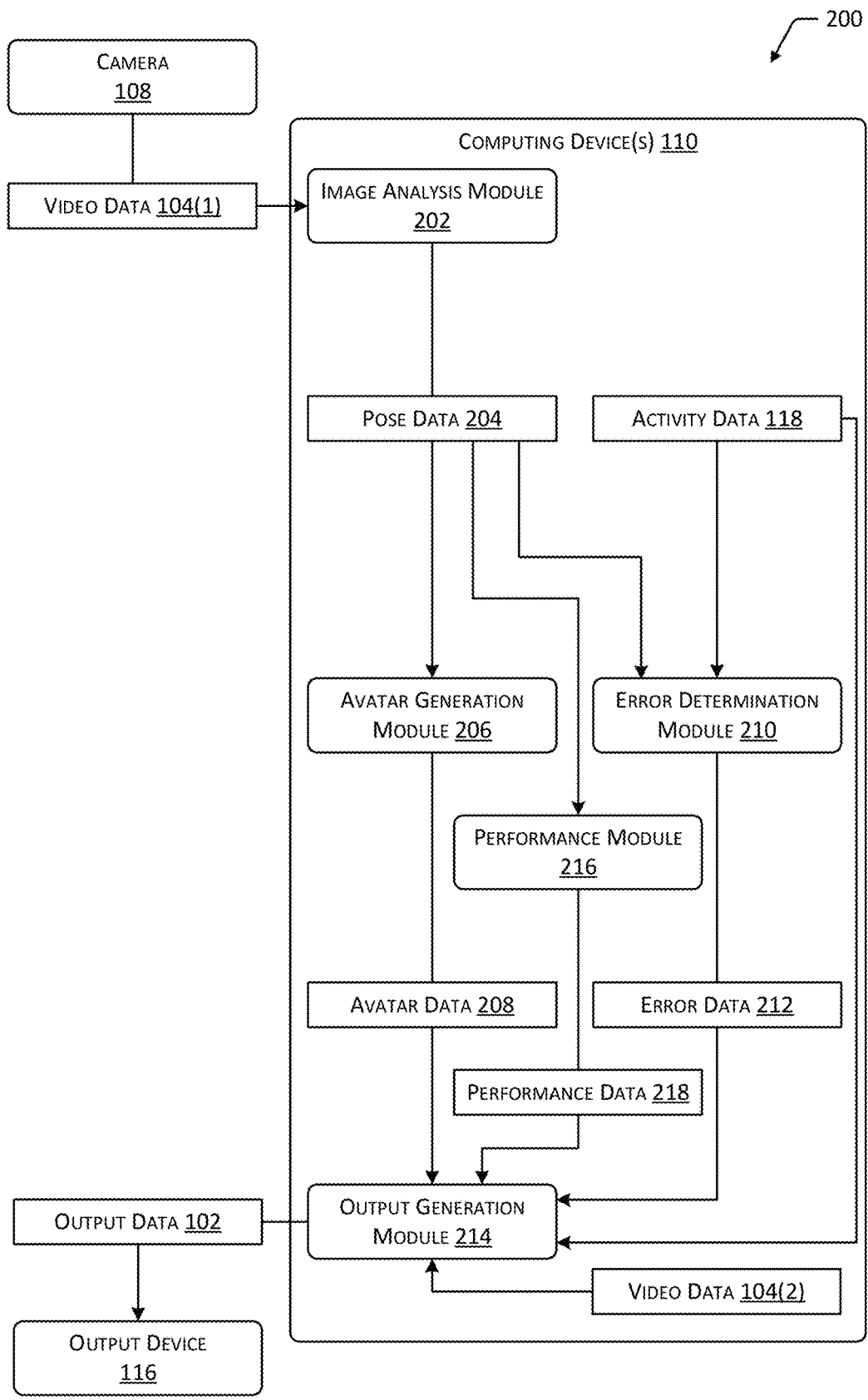
FIG. 2 depicts an implementation of a system for generating video output based on video data and activity data indicative of an activity being performed.

FIG. 2 depicts an implementation of a system 200 for generating video output based on video data 104 and activity data 118 indicative of an activity being performed. As described with regard to FIG. 1, video data 104(1) representing a user 106 performing an activity may be acquired using one or more cameras 108. Cameras 108 may include RGB cameras, depth cameras, IR cameras, or any other type of sensor able to acquire the video data 104(1). The video data 104(1) may include one or more still images or one or more frames of a video. The video data 104(1) may be sent from the camera 108 to one or more servers 110 or other computing devices. In other implementations, the camera 108 may be configured to perform one or more of the processes described herein.

An image analysis module 202 associated with the server(s) 110 may analyze the video data 104(1) to determine pose data 204 representative of the pose of the user 106 within the field of view of the camera 108. The image analysis module 202 may include one or more object recognition or segmentation algorithms to identify portions of acquired images or frames of video data 104(1) in which the user 106 is visible. For example, a segmentation algorithm may determine portions of a frame of video data 104(1) associated with a foreground, a background, the user 106, one or more other objects, and so forth. An object recognition algorithm may determine portions of a frame of video data 104(1) that correspond to particular body parts of the user 106, such as locations of the user's head, elbows, hips, knees, and so forth. As described previously, the determined locations of parts of the user's body may be represented as a set of points, and the location of one or more points may be constrained by the location of one or more other points based on a set of rules. For example, the location of a point representing a user's foot may be constrained based on the location of a point representing the user's knee, and vice versa.

An avatar generation module 206 associated with the server(s) 110 may generate avatar data 208 based on the pose data 204. The avatar data 208 may be used to generate a first avatar 112 representative of the pose of the user 106. For example, the avatar generation module 206 may generate an image having body parts in positions that correspond to the locations, joint angle, or body part rotation indicated in the pose data 204. In some implementations, the avatar generation module 206 may provide the image of the human form with a shape that corresponds to a shape of the user 106 determined based on the video data 104. In other implementations, the first avatar 112 may be provided with a default form or shape having body parts in positions that correspond to the pose data 204.

An error determination module 210 associated with the server(s) 110 may determine one or more differences between the pose data 204 that represents the pose of the user 106 and activity data 118 that includes one or more poses representative of correct performance of the activity. In some implementations, the error determination module 210 may use a neural network or other type of machine learning algorithm to classify the pose of the user 106 indicated in the pose data 204 using one or more poses of the activity data 118 as inputs. For example, the activity data 118 may include one or more poses indicative of correct performance of the activity, one or more poses indicative of incorrect performance of the activity, or poses indicative of both correct and incorrect performance of the activity. Classification of the differences between the pose of the user 106 and the activity data 118 may include determining how closely the pose of the user 106 corresponds to or differs from one or more correct or incorrect poses of the activity data 118. In other implementations, the error determination module 210 may determine differences between the pose data 204 that represents the pose of the user 106 and activity data 118 representing one or more correct poses by directly comparing the pose of the user 106 to the correct pose(s) of the activity data 118. Based on the pose data 204 and the activity data 118, the error determination module 210 may generate error data 212 indicative of one or more differences between the pose of the user 106 and the pose(s) indicated in the activity data 118.

An output generation module 214 associated with the server(s) 110 may generate output data 102 based on the avatar data 208, the error data 212, the activity data 118, and in some cases, additional video data 104(2). For example, during performance of an activity by a user 106, the output generation module 214 may generate output data 102 for presenting a first avatar 112 representative of the pose of the user 106 and a second avatar 114 based on additional video data 104(2). As described with regard to FIG. 1, the video data 104(2) may include a prerecorded video in which a second avatar 114 representing an instructor performs the activity correctly for the purpose of instructing the user 106. If the user 106 commits one or more errors while performing the activity, the error data 212 may indicate one or more differences between the pose of the user 106 and the pose(s) indicated in the activity data 118. The activity data 118 may indicate particular body parts of the user 106 or portions of the first avatar 112 that are associated with particular differences indicated in the error data 212. The activity data 118 may also indicate a priority value or hierarchy value associated with one or more differences. The activity data 118 may additionally indicate particular differences for which output is to be presented during performance of the activity, or for which output is to be presented after cessation of the activity. For example, the activity data 118 may indicate that during performance of a squat exercise, errors associated with the position of a user's knees have a higher priority than errors associated with the position of a user's arms. In such a case, if the error data 212 indicates errors associated with the arms and the knees of the user 106, based on the activity data 118, the output generation module 214 may generate output data 102 for presenting a portion of the first avatar 112 representing the user's knees and an instruction 122 regarding the error. As another example, the activity data 118 may indicate that output indicating errors associated with the position of a user's knees is to be presented during performance of the activity while output indicating errors associated with the position of a user's hips is to be presented after cessation of the activity. In such a case, if the error data 212 indicates errors associated with the knees and the hips of the user 106, during performance of the activity, the output generation module 214 may generate output data 102 for presenting a portion of the first avatar 112 representing the user's knees and an instruction 122 regarding the error. After performance of the activity has ceased, the output generation module 214 may generate output data 102 for presenting a portion of the first avatar 112 representing the user's hips and an instruction 122 regarding this error.

In some implementations, the activity data 118 may also indicate one or more values or rules associated with particular differences or with particular body parts of the user 106 that may be used to determine a score for performance of the activity by the user 106. For example, the score may include a value ranging from 0 to 100, with each difference between the poses achieved by the user 106 and the correct pose(s) indicated in the activity data 118 resulting in a modification to the score based on the magnitude of the difference, the priority of the difference indicated in the activity data 118, and so forth. In some implementations, after cessation of the activity, the output generation module 214 may generate output data 102 for presenting the score. In some cases, in response to user input, particular errors associated with different portions of the score may be presented. In some implementations, after cessation of the activity, the output generation module 214 may generate output data 102 for presenting a user interface that enables navigation between different errors associated with performance of the activity by the user 106. For example, the user interface may be used to navigate between video clips or images that depict portions of the activity during which one or more differences were determined between the poses of the user 106 and the pose(s) of the activity data 118. The particular number of differences included in the user interface and the particular differences that are presented may be determined based on the activity data 118. For example, for a particular activity, the activity data 118 may indicate that video clips showing the three differences associated with the greatest magnitude between the pose of the user 106 and the pose(s) of the activity data 118 are to be presented in a user interface.

Figure 3:
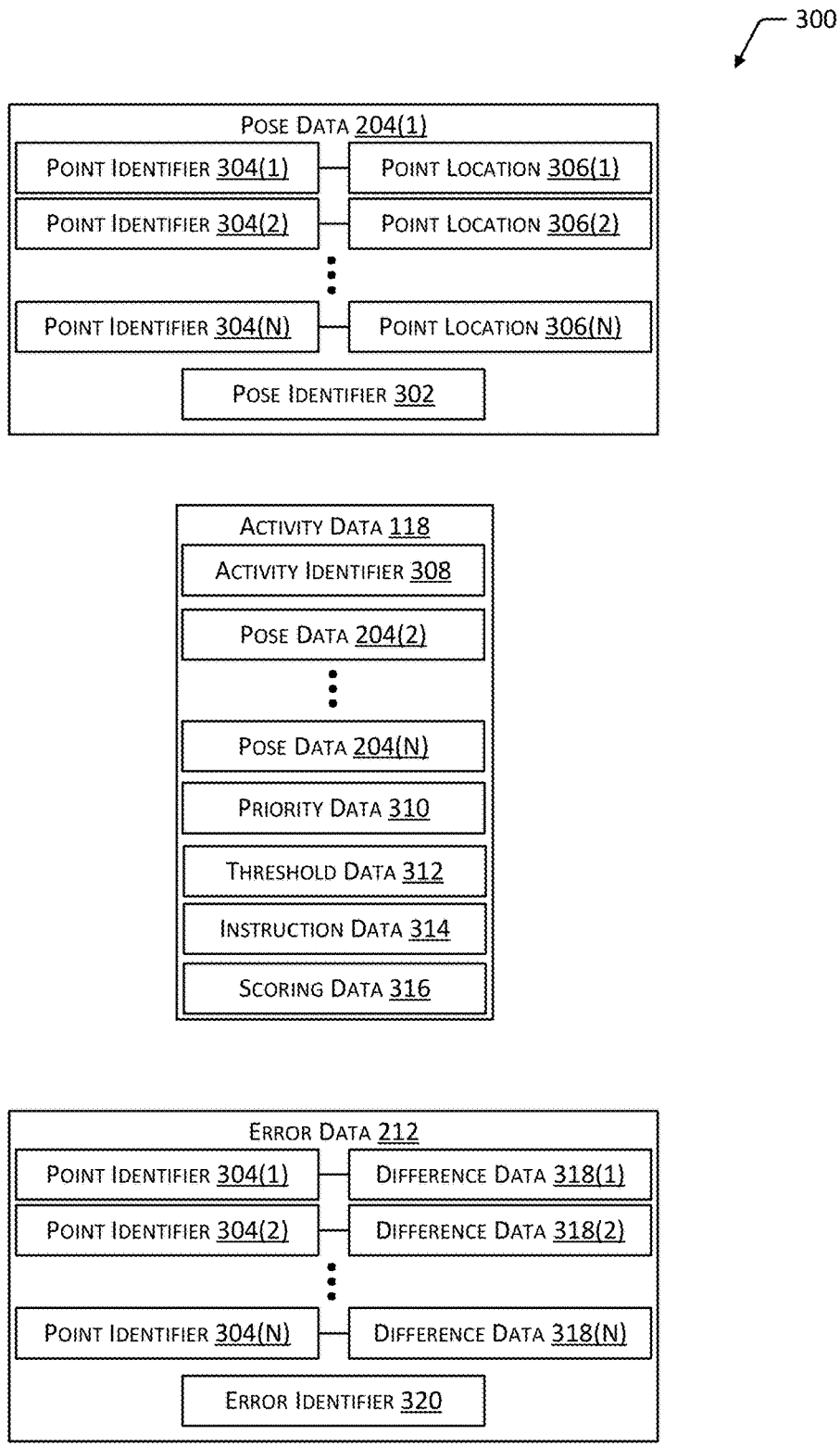
FIG. 3 is a series of block diagrams illustrating implementations of pose data, activity data, and error data.

FIG. 3 is a series of block diagrams 300 illustrating implementations of pose data 204, activity data 118, and error data 212. Pose data 204 may include data representative of the pose of a user 106, which may be determined based on one or more images or frames of video data 104. For example, a camera 108 may acquire video data 104 representing a user 106 within the field of view of the camera 108, and an image analysis module 202 may be used to determine pose data 204 based on the video data 104. The pose data 204 for a particular pose may be associated with a pose identifier 302, such as a name, number, or other data that may be used to differentiate particular pose data 204 from pose data 204 associated with other poses. The pose data 204 may represent the pose of a user 106 as a set of points, each point associated with a point identifier 304 and a point location 306 representative of the position of a point within an image or frame of video data 104. For example, a point identifier 304 may include an indication of a body part, such as the elbow of a user 106. In other cases, a point identifier 304 may include a name, number, alphanumeric string, or other type of data that may be used to differentiate a particular point from other points. A point location 306 may be expressed as a coordinate location within an image or frame of video data 104. In other implementations, a point location 306 may be expressed relative to an edge of the image or frame, relative to an origin point of the image or frame, or relative to a location of another point indicated in the pose data 204.

FIG. 3 depicts example pose data 204(1) in which a first point identifier 304(1) is associated with a first point location 306(1), a second point identifier 304(2) is associated with a second point location 306(2), and any number of additional point identifiers 304(N) are associated with any number of additional point locations 306(N). In some implementations, a pose of a user 106 may be represented by pose data 204(1) that includes thirty points, in which the point location 306 of each point represents the location of a body part of the user 106. In addition to pose data 204(1) determined based on video data 104 indicative of a user 106 performing an activity, other pose data 204(2) may include stored or pre-existing pose data 204(2). For example, the activity data 118 may include one or more sets of additional pose data 204(N) that represent correct or incorrect performance of the activity.

Activity data 118 may include data specific to a particular activity, or group of activities, that may be used to determine correct or incorrect performance of the activity, which errors to present to a user 106, the specific information that is presented regarding each error, how many errors to present to the user 106, the times at which the information regarding the errors is presented, and so forth. An activity identifier 308 associated with the activity data 118 may be used to differentiate particular activity data 118 from other activity data 118 that is associated with different activities. For example, the activity identifier 308 may include a name of an activity, a number, or other data that is specific to the particular activity data 118.

The activity data 118 may also include one or more sets of pose data 204. For example, FIG. 3 depicts the activity data 118 including second pose data 204(2) and any number of additional sets of pose data 204(N). Each pose data 204 associated with the activity data 118 may represent a pose associated with correct performance of the activity or a pose associated with incorrect performance of the activity. Each pose data 204 may be stored in association with an indication regarding whether the pose data 204 represents correct or incorrect performance of the activity. The pose data 204 may be used to determine whether a pose achieved by a user 106 corresponds to correct or incorrect performance of the activity. For example, pose data 204(1) determined based on video data 104 acquired from a user 106 may be compared to one or more sets of pose data 204 associated with the activity data 118 to determine one or more differences that may constitute errors committed by the user 106.

The activity data 118 may also include priority data 310. The priority data 310 may include one or more priority values that are associated with particular sets of pose data 204, or with particular body parts (e.g., particular points within a set of pose data 204). For example, activity data 118 associated with a squat exercise may include priority data 310 indicating a high priority value associated with points corresponding to locations of a user's knees and a lower priority value associated with positions corresponding to locations of a user's hands. The priority data 310 may be used to determine which errors are presented to a user 106, the order in which errors are presented, and so forth. In some implementations, priority data 310 may also indicate a time at which information regarding an error is presented. For example, a particular priority value may indicate that information regarding an error is to be presented during performance of an activity, while other priority values may indicate that information regarding an error is to be presented after cessation of the activity.

The activity data 118 may additionally include threshold data 312. Threshold data 312 may indicate particular priority values that are to be exceeded before information regarding an error is presented to a user 106. For example, if the activity data 118 indicates a low priority value for an error associated with the position of a user's head, and the priority value is less than a threshold value, information regarding the error may not be presented. However, if the priority value exceeds a threshold value, information regarding the error may be presented. Threshold data 312 may also indicate a threshold magnitude of a difference between a pose of a user 106 and a pose indicative of correct performance of an activity. If the magnitude of a difference between the location of a body part of the user 106 and a location indicative of correct performance of the activity exceeds a threshold value, information regarding the error may be presented. Threshold data 312 may additionally indicate a minimum or maximum count of errors that may be presented to a user, such as after cessation of an activity. For example, the threshold data 312 may indicate that information regarding the three errors having the highest priority values is to be presented in a user interface after cessation of the activity, while information regarding other errors is not presented.

The activity data 118 may also include instruction data 314. Instruction data 314 may include one or more audio or text instructions 122 that may be presented in association with a particular error, one or more error indications 124 associated with the error, and a body part or portion of an avatar associated with the error. For example, the instruction data 314 may be used to determine a particular portion of a first avatar 112 representative of a body part of the user 106 to be presented, and any text instructions 122, arrows, lines, or other error indications 124 that may be presented in conjunction with the avatar portion 120.

The activity data 118 may additionally include scoring data 316. Scoring data 316 may include one or more values, rules, algorithms, and so forth that may be used to determine one or more scores associated with performance of an activity by a user 106. For example, a score may be determined based on values associated with one or more poses, locations of points within a pose, particular errors, body parts, and so forth. In some implementations, a score may be determined based on values indicated in the priority data 310. For example, a score may include a value ranging from 0 to 100 that is determined based in part on error data 212 indicative of differences between poses achieved by the user 106 and pose data 204 indicative of correct performance of the activity. The error data 212 may include an indication of particular body parts (e.g., specific points within a set of pose data 204), a magnitude of the difference between the position of a body part of the user 106 and a correct position indicated in the pose data 204, and so forth. The activity data 118 may include a scoring value that may be used to weight or otherwise determine a final score based on one or more errors indicated in the error data 212.

Error data 212 may include data indicative of differences between a position of one or more body parts of a user 106, determined based on pose data 204(1) associated with the user 106, and positions of corresponding body parts, determined based on pose data 204 associated with the activity data 118. For example, error data 212 may associate a point identifier 304 for a particular point of the pose data 204(1) with difference data 318 indicative of a magnitude of a difference between the point location 306 for the particular point and one or more corresponding points indicated in the activity data 118. Continuing the example, a point representing the location of a user's right elbow may be classified by a neural network, using multiple poses indicative of correct performance of the activity as inputs. The difference data 318 may indicate a severity of the error committed by the user 106, which may be determined based in part on the magnitude of the difference between the location of the point representing the user's right elbow and the point(s) representing a location associated with correct performance of the activity. For example, if a user's elbow is bent at an angle that differs significantly from an angle associated with correct performance of the activity, the difference data 318 associated with the point representing the user's elbow may indicate a large difference. If the user's elbow is positioned in a manner that differs only slightly from a position or angle associated with correct performance of the activity, the difference data 318 may indicate a small difference. In some implementations, the difference data 318 may indicate values for each point associated with a user's pose. For example, difference data 318 may indicate a severity value ranging from 0 to 4 for each of thirty points representing the pose of a user 106. A value of 4 may indicate that the location of a point differs significantly from a location associated with correct performance of the activity, while a value of 0 may indicate that the location of a point corresponds to a location associated with correct performance of the activity. The difference data 318 may be used to determine particular errors for which information is presented to a user 106, the times at which the information is presented, and the manner in which a score for performance of the activity by the user 106 is calculated. In some implementations, error data 212 may also include one or more error identifiers 320 that may be used to differentiate sets of point identifiers 304 and difference data 318 associated with a particular error from those associated with other errors.

Figure 4:
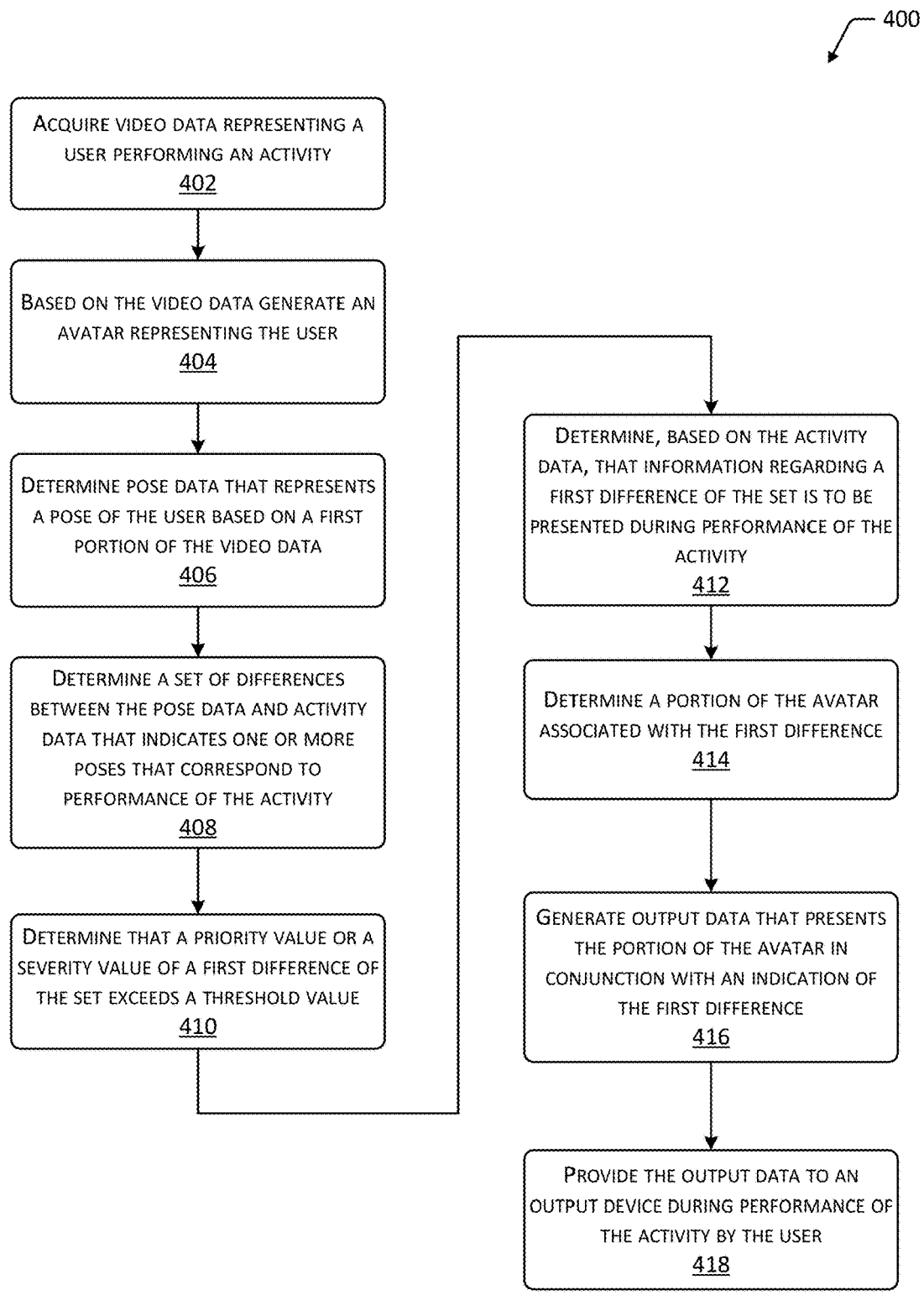
FIG. 4 is a flow diagram illustrating an implementation of a method for generating video output based on differences between a pose of a user performing an activity and poses that correspond to correct performance of the activity.

FIG. 4 is a flow diagram 400 illustrating an implementation of a method for generating video output based on differences between a pose of a user 106 performing an activity and poses that correspond to correct performance of the activity. At 402, video data 104 representing a user 106 performing an activity is acquired. For example, one or more cameras 108 may be used to acquire video data 104 while a user 106 within the field of view of the camera(s) 108 performs a fitness exercise or other type of activity.

At 404, based on the video data 104, an avatar representing the user 106 may be generated. As described with regard to FIGS. 1 and 2, a pose of the user 106 may be determined. The pose may represent the location and orientation of one or more body parts of the user 106. Based on this pose, an image of the avatar having body parts in positions and orientations that correspond to the locations and orientations of the pose may be generated. In some implementations, a first avatar 112 that represents the user 106 may be presented adjacent to a second avatar 114 that represents correct performance of the activity. For example, the second avatar 114 may be determined based on a prerecorded video that depicts the second avatar 114 or a human instructor performing the activity.

At 406, pose data 204 that represents a pose of the user 106 may be determined based on a first portion of the video data 104. For example, one or more servers 110 or other computing devices may use object recognition or segmentation algorithms to identify portions of an image or frame of video data 104 that include a user 106. Portions that include a body part of a user 106 may be identified and represented as a set of points. For example, pose data 204 may associate point identifiers 304 for points that represent body parts of the user 106 with corresponding point locations 306.

At 408, a set of differences may be determined between the pose data 204 and activity data 118 that indicates one or more poses that correspond to correct performance of the activity. In some implementations, a neural network or other type of machine learning algorithm may classify differences between the pose of the user 106 indicated in the pose data 204 and one or more poses of the activity data 118 used as inputs. For example, as described with regard to FIG. 2, an error determination module 210 associated with the server(s) 110 may determine a set of differences between the pose data 204 and the poses of the activity data 118 and generate error data 212 indicative the differences.

At 410, a determination may be made that a priority value or a severity value of a first difference of the set of differences exceeds a threshold value. For example, the activity data 118 associated with the activity may include priority data 310, such as one or more priority values associated with particular body parts, points of the pose data 204, or differences between the pose of the user 106 and the poses of the activity data 118. As another example, the error data 212 may include difference data 318 indicative of a magnitude of a difference between a location of a point representing a body part of the user 106 and a point representing a correct position of the body part indicated in the activity data 118. The activity data 118 may include threshold data 312 that specifies one or more threshold values associated with a priority or severity of a difference. For example, information regarding differences associated with a priority value of greater than a threshold may be presented to the user 106 while information regarding other differences is not presented. As another example, information regarding differences associated with difference data 318 that indicates a magnitude greater than a threshold may be presented, while information regarding other differences is not presented.

At 412, based on the activity data 118, a determination may be made that information regarding a first difference of the set of differences is to be presented during performance of the activity. For example, the activity data 118 may indicate that information regarding particular differences is to be presented during performance of the activity, while other information is to be presented after cessation of the activity. In other cases, the activity data 118 may indicate particular differences for which information is to be presented during performance of the activity, and for differences not indicated in the activity data 118, information may be presented after cessation of the activity. In still other cases, the activity data 118 may indicate particular differences for which information is to be presented after cessation of the activity, and for differences not indicated in the activity data 118, information may be presented during performance of the activity.

At 414, a portion of the avatar that is associated with the first difference may be determined. For example, the error data 212 may associate a point identifier 304 associated with a point representing a particular body part of the user 106 with difference data 318. Based on the point(s) indicated in the error data 212, the body part(s) of the user 106 associated with the error and the corresponding portion of the avatar that represents the body part(s) may be determined.

At 416, output data 102 for presenting the portion of the avatar may be generated, in conjunction with an indication of the first difference. For example, video output based on the output data 102 may present an avatar portion 120 representing the body part of the user 106 associated with the first difference, adjacent to an instruction 122 and one or more error indications 124 indicative of the first difference.

At 418, the output data 102 may be provided to an output device 116 for presentation. Based on the activity data 118 indicating that information regarding the difference is to be presented during performance of the activity, video output associated with the output data 102 may be presented during performance of the activity by the user 106.

Figure 5:
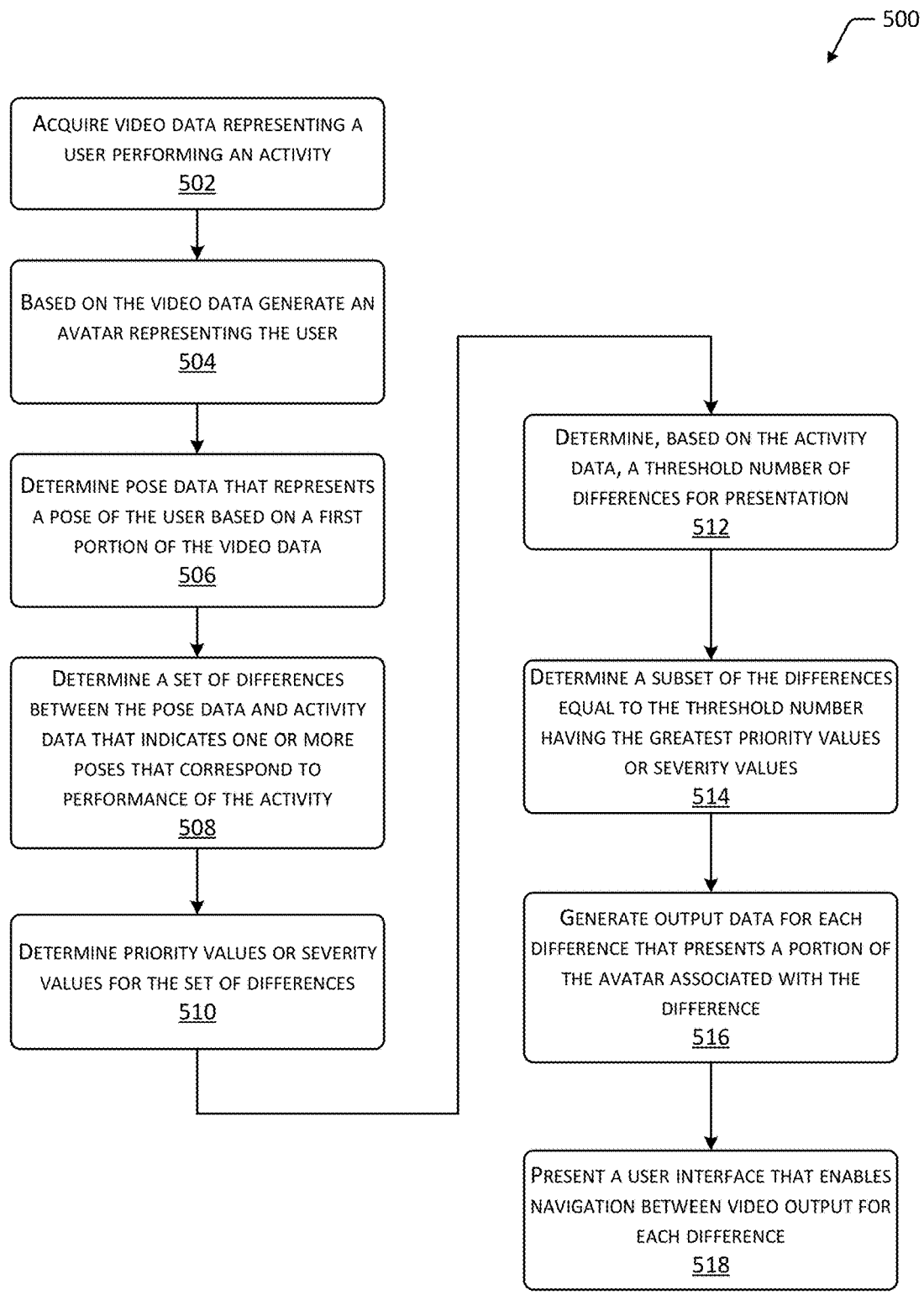
FIG. 5 is a flow diagram illustrating an implementation of a method for generating a user interface presenting information regarding multiple differences between a pose of a user and poses that correspond to correct performance of an activity.

FIG. 5 is a flow diagram 500 illustrating an implementation of a method for generating a user interface presenting information regarding multiple differences between a pose of a user 106 and poses that correspond to correct performance of an activity. At 502, video data 104 representing a user 106 performing an activity may be acquired. At 504, an avatar representing the user 106 may be generated based on the video data 104. At 506, pose data 204 that represents a pose of the user 106 may be determined based on a first portion of the video data 104.

At 508, a set of differences may be determined between the pose data 204 and activity data 118 that indicates one or more poses that correspond to correct performance of the activity. As described with regard to FIGS. 2 and 4, in some implementations, a neural network or other type of machine learning algorithm may be used to classify the differences between the pose of the user 106 indicated in the pose data 204 and one or more poses of the activity data 118 used as inputs. In other implementations, the pose of the user 106 may be compared to one or more poses that represent correct performance of the activity. In still other implementations, portions of the pose data 204 representing the pose of the user 106 may be compared to corresponding portions of poses indicated in the activity data 118. For example, a point representing a location of a user's elbow may be compared to a corresponding point representing a correct location of an elbow for correct performance of the activity.

At 510, priority values or severity values may be determined for the set of differences. As described with regard to FIG. 4, in some implementations, activity data 118 may indicate one or more priority values associated with particular body parts, particular points of the pose data 204, or particular differences between the pose of the user 106 and the poses of the activity data 118. In some cases, a severity value may be determined based on a magnitude of a difference between a location of a point representing a body part of the user 106 and a point representing a correct position of the body part indicated in the activity data 118.

At 512, based on the activity data 118, a threshold number of differences for presentation may be determined. For example, activity data 118 may include threshold data 312 indicative of a maximum number of differences to be presented in a user interface. Continuing the example, activity data 118 associated with a squat exercise may indicate that information regarding a maximum of three differences between the pose of a user 106 and the poses of the activity data 118 is to be presented. In such a case, the three differences of the set of differences having the largest severity values, or the largest priority values, or a combined value based on the priority and severity values, may be determined and presented in a user interface. For example, at 514, a subset of the differences equal to the threshold number may be determined. The subset of differences may include the greatest priority values or the greatest severity values of the set of differences.

At 516, output data 102 is generated for each difference. Each output data 102 may cause presentation of a video output of a portion of the avatar associated with the corresponding difference. For example, video output for a first difference associated with a position of a user's elbow may include an enlarged portion of the avatar that shows the position of the elbow. Video output for a second difference associated with a position of the user's knees may include an enlarged portion of the avatar that shows the position of the knees.

At 518, a user interface may be provided that enables navigation between the video output for each difference. For example, a user interface may include controls for selecting a particular video output for viewing. In some implementations, the user interface may be generated in response to determining, based on the activity data 118, that information regarding the particular differences represented in the user interface is to be presented after cessation of the activity. In other implementations, information regarding each difference of the determined subset may be presented in the user interface independent of whether the difference is indicated in the activity data 118. In some cases, information regarding a difference may be presented both during performance of an activity and in a user interface after cessation of the activity.

Figure 6:
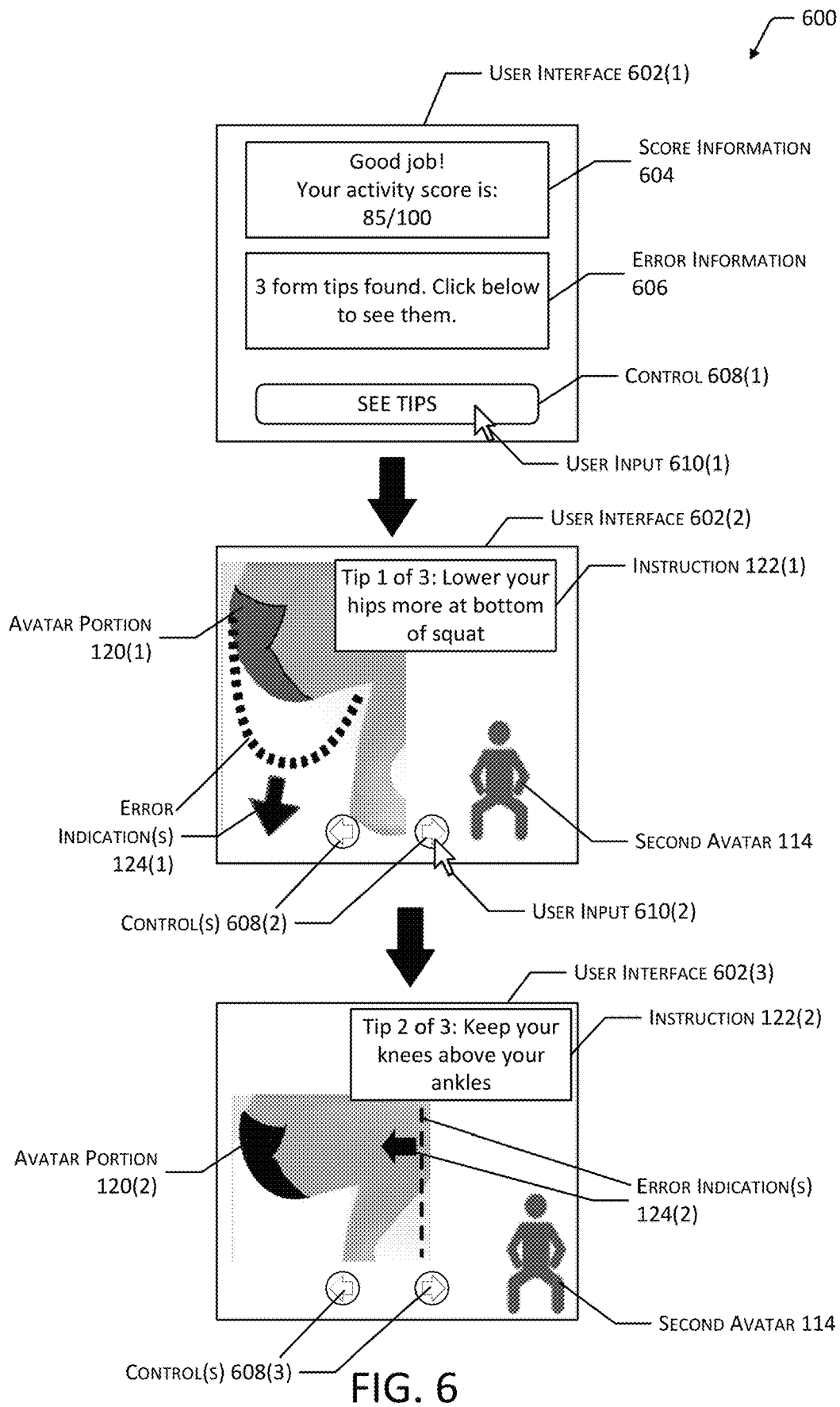
FIG. 6 is a diagram illustrating example user interfaces that may be used to present information regarding differences between a pose of a user and poses that correspond to correct performance of an activity.

FIG. 6 is a diagram 600 illustrating example user interfaces 602 that may be used to present information regarding differences between a pose of a user 106 and poses that correspond to correct performance of an activity. A first user interface 602(1) may be presented subsequent to cessation of an activity by the user 106. Cessation of the activity may include a determination that the user 106 has ceased movement or participation in the activity, a command or other indication from the user 106 to end performance of the activity, or completion of the output of instructional content. Cessation of the activity may also include completion of an activity by the user 106, such as performing a selected number of repetitions of a fitness exercise or performing the activity for a selected length of time.

As described with regard to FIG. 3, in some implementations, a score associated with performance of the activity may be presented. For example, the first user interface 602(1) includes score information 604 that presents a score value associated with performance of the activity. In some implementations, the score may include a numerical value that is lower for each error committed by the user 106. For example, correct performance of each pose associated with an activity may result in a high score value, while commission of a large number of errors may result in a low score value. In some cases, the severity of an error, such as the magnitude of a difference between the position of a body part of the user 106 and a correct position of the body part, may affect the score value. Additionally, in some cases, the activity data 118 may indicate particular errors that are to be disregarded, errors that have a large impact on a score value, errors that have a small impact on a score value, and so forth. For example, a priority value associated with a difference between the position of a body part of the user 106 and a correct position of the body part may affect the manner in which this difference modifies the score value.

The first user interface 602(1) may also include error information 606 that may indicate one or more differences between the poses achieved by the user 106 and poses associated with correct performance of the activity. For example, the error information 606 may indicate a number of errors for which information may be presented by navigating to other user interfaces 602 and an instruction for accessing this information.

The first user interface 602(1) may also include one or more controls 608(1), such as a button or other type of control 608(1). The control(s) 608(1) may be used to navigate to other user interfaces 602, cease presentation of the first user interface 602, and so forth. For example, FIG. 6 depicts first user input 610(1) actuating the control 608(1). In response to the first user input 610(1), a second user interface 602(2) may be presented.

The second user interface 602(2) may present video output associated with a first difference between a pose of the user 106 and one or more poses indicated in the activity data 118. For example, the second user interface 602(2) is shown presenting an avatar portion 120(1) that corresponds to a position of the hips of the user 106. An instruction 122(1) is positioned adjacent to the avatar portion 120(1). The instruction 122(1) includes text identifying that the information being presented corresponds to a first error of three total errors (e.g., "Tip 1 of 3"). The instruction 122(1) also includes information regarding the error, such as text instructing the user 106 to modify a position of the hips. The second user interface 602(2) also includes error indications 124(1), such as lines or arrows, that indicate the correct position of a body part relative to the position of the body part represented by the avatar portion 120(1). In some implementations, the second user interface 602(2) may also include the second avatar 114. The second avatar 114 may be used to demonstrate a pose associated with correct performance of the activity. For example, presenting the second avatar 114 adjacent to the avatar portion 120(1), instruction 122(1), and error indications 124(1) may facilitate comprehension by the user 106 regarding correction of the error.

The second user interface 602(2) may also include one or more controls 608(2) that may be used to navigate to additional user interfaces 602 or the previous first user interface 602(1). For example, FIG. 6 depicts the second user interface 602(2) including two buttons having arrows indicating the functionality of the buttons to navigate to successive and preceding user interfaces 602. In response to user input 610(2) to one of the controls 608(2), a third user interface 602(3) may be presented. In some implementations, the second user interface 602(2) may also be configured to receive user input 610 to a region that presents the avatar portion 120(1) or to one or more controls 608 for controlling the displayed avatar portion 120(1). For example, a user 106 may provide user input 610 to magnify or reduce (e.g., zoom in or zoom out) the size of the avatar portion 120 that is displayed, rotate or translate the viewpoint shown in the user interface 602(2), and so forth.

The third user interface 602(3) is shown presenting information regarding a different error, as indicated in the instruction 122(2) (e.g., "Tip 2 of 3"). Information regarding this different error may include a different avatar portion 120(2) representing the body part of the user 106 associated with the error. The instruction 122(2) may include text instructing the user 106 to modify a position of the body part. The third user interface 602(3) may also include one or more error indications 124(2), such as lines or arrows, that indicate the position or direction in which one or more body parts of the user 106 may be moved to reduce the difference between the pose of the user 106 and the poses indicated in the activity data 118. In some implementations, the third user interface 602(3) may also present the second avatar 114, which may represent a pose associated with correct performance of the activity. The third user interface 602(3) may also include one or more controls 608(3) that may be used to navigate to additional or previous user interfaces 602. In some implementations, the third user interface 602(3) may include controls 608 or may be configured to receive user input 610 to magnify, reduce, translate, or rotate the displayed avatar portion 120(2).

Figure 7:
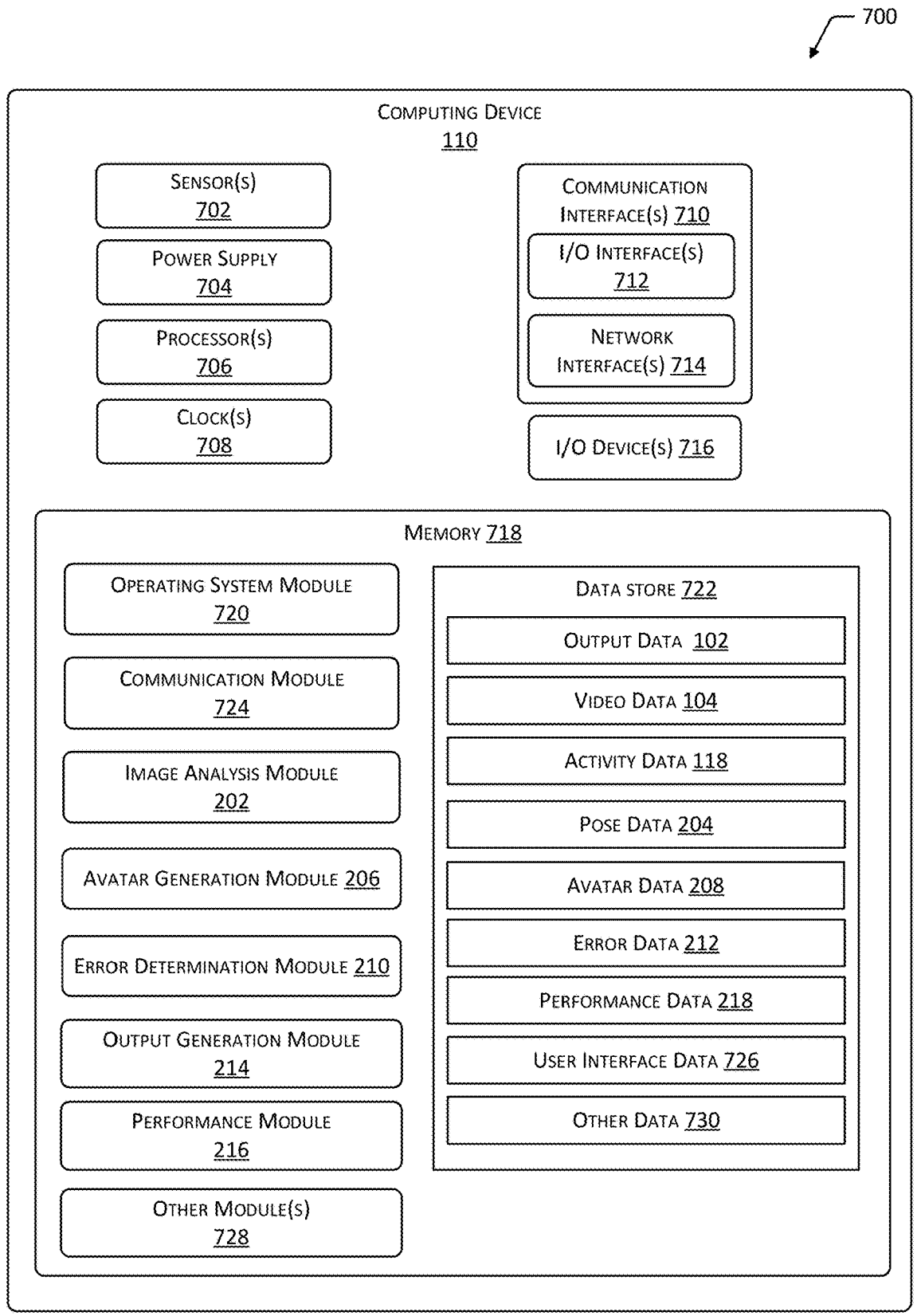
FIG. 7 is a block diagram illustrating an implementation of a computing device within the present disclosure.

FIG. 7 is a block diagram 700 illustrating an implementation of a computing device 702 within the present disclosure. The computing device 702 may include a server 110, a computing device 702 associated with a camera 108, a computing device 702 associated with an output device 116, or any other computing device 702 in communication with a server 110, camera 108, or output device 116. Additionally, while FIG. 7 depicts a single block diagram 700 of a computing device 702, any number and any type of computing devices 702 may be used to perform the functions described herein.

One or more power supplies 704 may be configured to provide electrical power suitable for operating the components of the computing device 702. In some implementations, the power supply 704 may include a rechargeable battery, fuel cell, photovoltaic cell, power conditioning circuitry, and so forth.

The computing device 702 may include one or more hardware processor(s) 706 (processors) configured to execute one or more stored instructions. The processor(s) 706 may include one or more cores. One or more clock(s) 708 may provide information indicative of date, time, ticks, and so forth. For example, the processor(s) 706 may use data from the clock 708 to generate a timestamp, trigger a preprogrammed action, and so forth.

The computing device 702 may include one or more communication interfaces 710, such as input/output (I/O) interfaces 712, network interfaces 714, and so forth. The communication interfaces 710 may enable the computing device 702, or components of the computing device 702, to communicate with other computing devices 702 or components of the other computing devices 702. The I/O interfaces 712 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 712 may couple to one or more I/O devices 716. The I/O devices 716 may include any manner of input devices or output devices associated with the computing device 702. For example, I/O devices 716 may include touch sensors, displays, touch sensors integrated with displays (e.g., touchscreen displays), keyboards, mouse devices, microphones, image sensors, cameras, scanners, speakers or other types of audio output devices, haptic devices, printers, and so forth. In some implementations, the I/O devices 716 may be physically incorporated with the computing device 702. In other implementations, the I/O devices 716 may be externally placed. The I/O devices 716 may also include one or more sensors, that may be in direct or wireless communication with the computing device 702. For example, various types of sensors may be worn or carried by a user 106, integrated within an object within an environment with the computing device 702 or user 106, and so forth.

The network interfaces 714 may be configured to provide communications between the computing device 702 and other devices, such as the I/O devices 716, routers, access points, and so forth. The network interfaces 714 may include devices configured to couple to one or more networks including local area networks (LANs), wireless LANs (WLANs), wide area networks (WANs), wireless WANs, and so forth. For example, the network interfaces 714 may include devices compatible with Ethernet, Wi-Fi, Bluetooth, ZigBee, Z-Wave, 3G, 4G, 5G, LTE, and so forth.

The computing device 702 may include one or more busses or other internal communications hardware or software that allows for the transfer of data between the various modules and components of the computing device 702.

As shown in FIG. 7, the computing device 702 may include one or more memories 718. The memory 718 may include one or more computer-readable storage media (CRSM). The CRSM may be any one or more of an electronic storage medium, a magnetic storage medium, an optical storage medium, a quantum storage medium, a mechanical computer storage medium, and so forth. The memory 718 may provide storage of computer-readable instructions, data structures, program modules, and other data for the operation of the computing device 702. A few example modules are shown stored in the memory 718, although the same functionality may alternatively be implemented in hardware, firmware, or as a system on a chip (SoC).

The memory 718 may include one or more operating system (OS) modules 720. The OS module 720 may be configured to manage hardware resource devices such as the I/O interfaces 712, the network interfaces 714, the I/O devices 716, and to provide various services to applications or modules executing on the processors 706. The OS module 720 may implement a variant of the FreeBSD operating system as promulgated by the FreeBSD Project; UNIX or a UNIX-like operating system; a variation of the Linux operating system as promulgated by Linus Torvalds; the Windows operating system from Microsoft Corporation of Redmond, Washington, USA; or other operating systems.

One or more data stores 722 and one or more of the following modules may also be associated with the memory 718. The modules may be executed as foreground applications, background tasks, daemons, and so forth. The data store(s) 722 may use a flat file, database, linked list, tree, executable code, script, or other data structure to store information. In some implementations, the data store(s) 722 or a portion of the data store(s) 722 may be distributed across one or more other devices including other computing devices 702, network attached storage devices, and so forth.

A communication module 724 may be configured to establish communications with one or more other computing devices 702. Communications may be authenticated, encrypted, and so forth.

The memory 718 may also store the image analysis module 202. The image analysis module 202 may analyze video data 104 or image data to determine pose data 204 representative of the pose of a user 106 within the video data 104 or image data. For example, one or more object recognition or segmentation algorithms may be used to identify portions of acquired images or frames of video data 104(1) in which a user 106 is visible. Object recognition algorithms may also be used to determine portions of images or frames of video data 104(1) that correspond to particular body parts of a user 106. As described previously, the determined locations and orientations of parts of the user's body may be represented as a set of points, and the location of one or more points may be constrained by the location of one or more other points based on a set of rules.

The memory 718 may additionally include the avatar generation module 206. The avatar generation module 206 may generate avatar data 208 based on the pose data 204. The avatar data 208 may be used for presentation of an avatar representative of the pose of a user 106. For example, the avatar generation module 206 may generate an image of a human form or other type of form having body parts in positions that correspond to the locations and orientations indicated in the pose data 204. In some implementations, the avatar generation module 206 may determine other characteristics of a user 106, such as a body shape, facial characteristics, color or shape of clothing worn, color or style of hair, and so forth, and may provide the avatar with one or more shapes, colors, or pieces of clothing that correspond to these characteristics of the user 106. In other implementations, an avatar may be provided with a default form or shape having body parts in positions that correspond to the pose data 204. The avatar may constitute a simulated three-dimensional shape. Therefore, when the avatar is displayed, a user 106 may view the avatar from different angles, enlarge or reduce the size of the view, and so forth. For example, a presented user interface 602 may receive user input 610 to translate, magnify, reduce, or rotate a view that presents an avatar.

The memory 718 may also store the error determination module 210. The error determination module 210 may determine one or more differences between the pose data 204 that represents the pose of a user 106 and activity data 118 that includes one or more poses representative of correct performance of an activity. In some implementations, the error determination module 210 may use a neural network or other type of machine learning algorithm to classify the pose of the user 106 indicated in the pose data 204 using one or more poses of the activity data 118 as inputs. In other implementations, the error determination module 210 may directly compare the locations of points of the pose data 204 with the locations of corresponding points in one or more other poses indicated in the activity data 118. Based on the pose data 204 and the activity data 118, the error determination module 210 may generate error data 212 indicative of one or more differences between the pose data 204 and the activity data 118.

The memory may additionally store the output generation module 214. The output generation module 214 may generate output data 102 based on avatar data 208, error data 212, and activity data 118. For example, during performance of an activity by a user 106, the output generation module 214 may generate output data 102 for presenting an avatar representative of the pose of the user 106. If the user 106 commits one or more errors while performing the activity, the error data 212 may indicate one or more differences between the pose of the user 106 and the pose(s) indicated in the activity data 118. The activity data 118 may indicate particular body parts of the user 106 or portions of the first avatar 112 that are associated with particular differences indicated in the error data 212. The activity data 118 may also indicate a priority or hierarchy associated with one or more differences. Based on the error data 212 and the activity data 118, the output generation module 214 may generate output data 102 for presenting a portion of the avatar representing a body part of the user 106 that is associated with the error, and one or more instructions 122 or error indications 124 providing information regarding the error. The output generation module 214 may also generate one or more user interfaces 602 for presenting information regarding errors committed by the user 106. In some implementations, the output generation module 214 may determine a score associated with performance of the activity by the user 106 based in part on the activity data 118 and the error data 212. In such a case, one or more user interfaces 602 may include score information 604 indicative of the score. The output generation module 214 may access user interface data 726, which may indicate various content and characteristics of user interfaces 602 to be generated, such as layouts, controls 608, and so forth.

Other modules 728 may also be present in the memory 718. For example, other modules 728 may include permission or authorization modules to enable a user 106 to provide authorization to acquire video data 104 of the user 106. Other modules 728 may also include encryption modules to encrypt and decrypt communications between computing devices 702, authentication modules to authenticate communications sent or received by computing devices 702, a permission module to assign, determine, and manage user permissions to access or modify data associated with computing devices 702, and so forth.

Other data 730 within the data store(s) 722 may include configurations, settings, preferences, and default values associated with computing devices 702. Other data 730 may also include encryption keys and schema, access credentials, and so forth. Other data 730 may additionally include audio files for output, such as during performance of activities by a user 106.

In different implementations, different computing devices 702 may have different capabilities or capacities. For example, servers 110 may have greater processing capabilities or data storage capacity than computing devices 702 associated with cameras 108 or output devices 116.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
an output device;
one or more memories storing computer-executable instructions; and
one or more hardware processors to execute the computer-executable instructions to:
acquire first video data representing a user performing an activity;
determine a first pose of the user based on the first video data;
generate an avatar representing the first pose of the user;
access activity data that indicates a second pose and a third pose, wherein the second pose and the third pose are indicative of correct performance of the activity;
determine a first difference between the first pose and the second pose;
determine, based on the activity data, that the first difference is associated with presentation of output during performance of the activity;
determine, based on the activity data, a first instruction associated with the first difference;
determine a first portion of the avatar associated with the first difference;
present, using the output device, first output that includes the first portion of the avatar at a first time during performance of the activity and excludes a second portion of the avatar, wherein the activity data associates the first difference with the first time;
present, using the output device, the first instruction at the first time;
acquire second video data representing the user performing the activity;

determine a fourth pose of the user based on the second video data;
determine a second difference between the third pose and the fourth pose;
determine, based on the activity data, that the second difference is associated with presentation of output after cessation of the activity;
determine, based on the activity data, a second instruction associated with the second difference;
determine a third portion of the avatar associated with the second difference;
determine cessation of the activity;
present, using the output device, second output that includes the third portion of the avatar at a second time subsequent to the cessation of the activity and excludes a fourth portion of the avatar, wherein the activity data associates the second difference with the second time; and
present, using the output device, the second instruction at the second time.

2. The system of claim 1, further comprising computer-executable instructions to:
determine the second pose based on a first plurality of poses associated with the correct performance of the activity; and
determine the third pose based on a second plurality of poses associated with the correct performance of the activity;
wherein the first difference is determined by comparing the first pose to the first plurality of poses; and
wherein the second difference is determined by comparing the fourth pose to the second plurality of poses.

3. A method comprising:
determining, based on first video data acquired at a first time, a first pose of a user performing an activity;
generating an avatar representing the first pose of the user;
determining, based on first data that indicates one or more second poses representing correct performance of the activity, a first difference between the first pose and the one or more second poses;
determining a first portion of the avatar associated with the first difference; and
presenting, using an output device at a second time, first output that includes the first portion of the avatar and an indication of the first difference and that excludes a second portion of the avatar.

4. The method of claim 3, further comprising:
determining, based on the first data, that the first difference is associated with presentation of output during performance of the activity, wherein the presenting of the first output is in response to the determining of the first difference, and wherein the second time occurs during performance of the activity.

5. The method of claim 3, further comprising:
determining, based on the first data, that the first difference is associated with presentation of output after cessation of the activity; and
determining the cessation of the activity, wherein the first output is presented in response to the cessation of the activity, and wherein the second time occurs after the cessation of the activity.

6. The method of claim 3, further comprising:
determining, based on second video data, a third pose of the user performing the activity;
determining cessation of the activity;
determining, based on the first data that further indicates one or more fourth poses indicative of the correct performance of the activity, a second difference between the third pose and the one or more fourth poses;
determining a third portion of the avatar associated with the second difference;
determining, based on the first data, that the first difference is associated with presentation of output during performance of the activity and the second difference is associated with presentation of output after the cessation of the activity, wherein the first output is presented during the performance of the activity; and
presenting a second output that includes the third portion of the avatar and an indication of the second difference after the cessation of the activity, wherein the second output excludes a fourth portion of the avatar.

7. The method of claim 3, further comprising:
receiving a plurality of poses associated with the correct performance of the activity; and
determining, using a machine learning module, the one or more second poses using the plurality of poses as inputs, wherein the first difference is determined by classifying the first pose based on similarity to one or more of the plurality of poses.

8. The method of claim 3, further comprising:
determining, based on the first pose, a first plurality of locations, wherein each location of the first plurality of locations is associated with a body part of the user represented in the first video data;
determining, based on the first data, a second plurality of locations associated with the correct performance of the activity; and
determining, based on correspondence between the first plurality of locations and the second plurality of locations, a plurality of differences that includes the first difference.

9. The method of claim 8, further comprising:
determining, based on the first data, that a priority value associated with the first difference is greater than one or more of: a threshold priority value or a priority value associated with at least one second difference of the plurality of differences;
wherein the first portion of the avatar and the indication of the first difference are presented based on the priority value associated with the first difference.

10. The method of claim 8, further comprising:
determining a severity value associated with the first difference based on a distance between a first location of the first plurality of locations and a second location of the second plurality of locations; and
determining that the severity value is greater than one or more of: a threshold severity value or a severity value associated with at least one second difference of the plurality of differences;
wherein the first portion of the avatar and the indication of the first difference are presented based on the severity value associated with the first difference.

11. The method of claim 8, further comprising:
determining a plurality of values based on the first data, wherein each value of the plurality of values is associated with a difference of the plurality of differences;
determining a score based on the plurality of values; and
presenting the score using the output device.

12. A system comprising:
one or more memories storing computer-executable instructions; and
one or more hardware processors to execute the computer-executable instructions to:

determine, at a first time and based on first video data, a first pose of a user performing an activity;

generate a first avatar representing the first pose of the user;

determine one or more second poses representing correct performance of the activity;

determine a first difference between the first pose and the one or more second poses;

determine a first portion of the first avatar that is associated with the first difference; and at a second time after the first time, present, using one or more output devices, first output that includes the first portion of the first avatar and excludes a second portion of the first avatar.

13. The system of claim 12, further comprising computer-executable instructions to:

at the first time, present the first avatar adjacent to a second avatar representing a second pose of the one or more second poses.

14. The system of claim 12, wherein the second time occurs after cessation of the activity by the user, the system further comprising computer-executable instructions to:

present at the second time and adjacent to the first portion of the first avatar, one or more of:

a second avatar representing a second pose of the one or more second poses; or a third portion of the second avatar that corresponds to the first difference.

15. The system of claim 12, further comprising computer-executable instructions to:

determine, at a third time after the first time and before the second time, a third pose of the user performing the activity;

determine one or more fourth poses representing correct performance of the activity;

determine a second difference between the third pose and the one or more fourth poses;

determine a third portion of the first avatar that is associated with the second difference; and at a fourth time after the third time and before the second time, present second output that includes the third portion of the first avatar and excludes a fourth portion of the first avatar using the one or more output devices, wherein the fourth time occurs prior to cessation of the activity by the user and the second time occurs subsequent to cessation of the activity by the user.

16. The system of claim 12, further comprising computer-executable instructions to:

determine, based on the first pose, a first plurality of locations, wherein each location of the first plurality of locations is associated with a body part of the user represented in the first video data;

determine, based on the one or more second poses, a second plurality of locations associated with the correct performance of the activity;

determine correspondence between the first plurality of locations and the second plurality of locations;

based on the correspondence, determine a plurality of differences that includes the first difference; and determine a value associated with each difference of at least a subset of the plurality of differences that includes the first difference, wherein the first difference is presented based on a first value associated with the first difference.

17. The system of claim 16, wherein the first value associated with the first difference is determined based in part on a distance between a first location of the first plurality of locations and a second location of the second plurality of locations.

18. The system of claim 16, further comprising computer-executable instructions to:

determine, based on first data associated with performance of the activity, a threshold count of differences and a threshold value for presentation of differences;

determine that the first value is greater than the threshold value; and determine that a count of differences that includes the first difference is less than the threshold count of differences;

wherein the first difference is presented based on the first value exceeding the threshold value and the count of differences being less than the threshold count of differences.

19. The system of claim 12, further comprising computer-executable instructions to:

receive user input indicating one or more body parts of the user; and determine that the first difference corresponds to a body part of the one or more body parts, wherein the first portion of the first avatar is presented based on the first difference corresponding to the body part of the one or more body parts.

20. The system of claim 12, further comprising computer-executable instructions to:

receive user input associated with the first portion of the first avatar, wherein the user input is associated with one or more of a magnification, a rotation, or a translation of the first avatar; and in response to the user input, present a second portion of the first avatar.

\* \* \* \* \*